United States Patent
Perez

(10) Patent No.: US 8,188,047 B2
(45) Date of Patent: May 29, 2012

(54) THERAPEUTIC AND COSMETIC COMPOSITIONS FOR TREATMENT OF SKIN

(76) Inventor: Thomas Perez, Chicago, IL (US)

( * ) Notice: Subject to any disclaimer, the term of this patent is extended or adjusted under 35 U.S.C. 154(b) by 44 days.

(21) Appl. No.: 12/408,341

(22) Filed: Mar. 20, 2009

(65) Prior Publication Data

US 2010/0240755 A1    Sep. 23, 2010

(51) Int. Cl.
*A61K 31/195*    (2006.01)
(52) U.S. Cl. .......................................... 514/18; 514/562
(58) Field of Classification Search .................. None
See application file for complete search history.

(56) References Cited

U.S. PATENT DOCUMENTS

| | | | | |
|---|---|---|---|---|
| 7,427,690 | B2 * | 9/2008 | Gupta | 562/440 |
| 2002/0058053 | A1 * | 5/2002 | Nakanishi et al. | 424/401 |
| 2006/0110415 | A1 * | 5/2006 | Gupta | 424/401 |
| 2006/0177430 | A1 * | 8/2006 | Bhushan et al. | 424/94.1 |

OTHER PUBLICATIONS

National Cancer Institute—www.cancer.gov, Melanoma treatment, Aug. 2010, pp. 1-3.*

* cited by examiner

*Primary Examiner* — Christopher R. Tate
*Assistant Examiner* — Roy Teller
(74) *Attorney, Agent, or Firm* — Adam K. Sacharoff

(57) ABSTRACT

The present invention is directed to a skin cream containing L-glutathione and methyl sulfone in combination with perfluorodecalin and various vitamins such as Vitamin D and C. The cream can be used to treat cancerous and precancerous diseases found in or on the skin.

4 Claims, No Drawings

THERAPEUTIC AND COSMETIC COMPOSITIONS FOR TREATMENT OF SKIN

BACKGROUND OF THE INVENTION

The present invention relates to therapeutic and cosmetic compositions for the treatment of cancer and skin including cancer diseases and/or precancerous stages such as those found in moles.

The treatment of cancer diseases and/or precancerous stages found in the skin or body is well documented, most of which relates around cutting out the infectious area and/or treating the area with radiation. Notwithstanding these well known and well defined treatments, there is always a continual need for additional treatment methods and products that can be used with such methods.

SUMMARY OF THE INVENTION

The present invention is directed to a skin cream containing L-glutathione and methyl sulfone in combination with perfluorodecalin and various vitamins such as Vitamin D and C. The cream can be used to treat cancerous and precancerous diseases found in or on the skin.

DETAILED DESCRIPTION OF THE INVENTION

The present invention includes a method and a product adapted to be used for the treatment of cancerous diseases and/or precancerous stages found in the skin or body.

The ingredients used to create the cream are preferably to include Vitamin D and a Vitamin D precursor, which acts as a catalyst and a substrate during metabolism. The cream may further include L-glutathione and methyl sulfone (also known as $DMSO_2$).

By way of background, L-glutathione is a master antioxidant and detoxifier. It protects tissues by neutralizing free radicals, and improves the immune system by promoting antigen presentation and stimulating CD8 cells. Glutathione is typically involved in various liver detoxification processes. In addition, methyl sulfone, when added to the cream, drivers the L-glutathione through the skin. It may also be possible to use dimethyl sulfoxide (DMSO) instead of methyl sulfone $DMSO_2$.

The cream may further include perfluorodecalin (C10F18), which is a fluorocarbon, a derivative of decalin in which all of the hydrogen atoms are replaced by fluorine atoms. Perfluorodecalin is chemically and biologically inert, and typically stable up to 400° C.

The cream has a base in which the aforementioned ingredients may be added. The base is preferably created from mixing diethylene glycol monoethyl ether, organic base component, and a hydrophilic base component. Diethylene glycol monoethyl ether is an industrial solvent. It is a clear, colorless, hygroscopic liquid. Structurally it is an alcohol and an ether. At direct contact it causes drying of skin by leaching fats.

EXAMPLE I

This example describes the preparation of a cream which has been used on cancerous skin diseases and may be used to treat breast cancer level 4 with *pseudomonas aureoginosa* (also known as *P. aeruginosa*). The base of the cream was made by mixing 2 ml of diethylene glycol monoethyl ether, 12 ml of a organic base component, and 36 ml of a hydrophilic base component. The base was mixed with 13.04 ml of perfluorodecalin and 2 grams of an Aloe Vera Powder. This is further mixed with 2 grams of L-glutathione and 2 grams of methyl sulfone. In addition, 0.1 ml of a Vitamin D precursor and 1 mg of Vitamin D are added to the mixture. The Vitamin D precursor in one embodiment may be 1a,25-dihydroxycholecalciferol. Lastly, 2 grams of N-acetyl-cysteine and 2 grams of ascorbic acid. The ingredients can be combined and mixed together to form a cream with a combined volume of about 63.14 ml. Applied daily, significant reduction in the cancerous cells and the *P. aeruginosa* was observed over a period of time 50 days.

To create the cream in any significant amounts, the following breakdown shown the active:

diethylene glycol monoethyl ether—about 0.032 milliliter per milliliter of said composition;

organic base component—about 0.019 milliliter per milliliter of said composition;

hydrophilic base component—about 0.57 milliliter per milliliter of said composition;

perfluorodecalin—about 0.21 milliliter per milliliter of said composition;

Aloe Vera Powder—about 31.75 milligrams per milliliter of said composition;

L-glutathione—about 31.75 milligrams per milliliter of said composition;

methyl sulfone—about 31.75 milligrams per milliliter of said composition;

Vitamin D precursor—about 0.002 milliliter per milliliter of said composition;

Vitamin D—about 0.016 milligrams per milliliter of said composition;

N-acetyl-cysteine—about 31.75 milligrams per milliliter of said composition; and ascorbic acid—about 31.75 milligrams per milliliter of said composition.

EXAMPLE II

This example describes the preparation of a cream which has been used on cancerous skin diseases and may be used to treat breast cancer level 4 with *pseudomonas aureoginosa* (also known as *P. aeruginosa*). The base of the cream was made by mixing 2 ml of diethylene glycol monoethyl ether, 12 ml of a organic base component, and 36 ml of a hydrophilic base component. The base was mixed with 13.04 ml of perfluorodecalin and 2 grams of an Aloe Vera Powder. This is further mixed with 2 grams of L-glutatione and 2 grams of methyl sulfone. In addition, 1 mg of Vitamin D are added to the mixture. Lastly, 2 grams of N-acetyl-cysteine and 2 grams of ascorbic acid. The ingredients can be combined and mixed together to form a cream with a combined volume of about 63.14 ml. To create the cream in any significant amounts, the following breakdown shown the active:

diethylene glycol monoethyl ether—about 0.032 milliliter per milliliter of said composition;

organic base component—about 0.019 milliliter per milliliter of said composition;

hydrophilic base component—about 0.57 milliliter per milliliter of said composition;

perfluorodecalin—about 0.21 milliliter per milliliter of said composition;

Aloe Vera Powder—about 31.75 milligrams per milliliter of said composition;

L-glutathione—about 31.75 milligrams per milliliter of said composition;

methyl sulfone—about 31.75 milligrams per milliliter of said composition;

Vitamin D—about 0.016 milligrams per milliliter of said composition;

N-acetyl-cysteine—about 31.75 milligrams per milliliter of said composition; and ascorbic acid—about 31.75 milligrams per milliliter of said composition.

From the foregoing and as mentioned above, it will be observed that numerous variations and modifications may be effected without departing from the spirit and scope of the novel concept of the invention. It is to be understood that no limitation with respect to the specific embodiments illustrated herein is intended or should be inferred. It is, of course, intended to cover by the appended claims all such modifications as fall within the scope of the claims.

I claim:

1. A skin cream composition comprising: perfluorodecalin, L-glutathione and dimethyl sulfoxide wherein said L-glutathione is present in an amount of at least about 31.75 milligrams per milliliter of said composition, said dimethyl sulfoxide is present in an amount of at least about 31.75 milligrams per milliliter, and said perfluorodecalin is present in an amount of at least about 0.21 milliliter per milliliter of said composition.

2. The composition according to claim 1, wherein the composition further includes a Vitamin D precursor and a Vitamin D.

3. The composition according to claim 2, wherein said Vitamin D precursor is present in an amount of at least about .002 milliliter per milliliter of said composition and said Vitamin D is present in an amount of at least about .016 milligrams per milliliter of said composition.

4. The composition according to claim 2, wherein the composition further includes N-acetyl-cysteine is present in an amount of about 31.75 milligrams per milliliter of said composition and ascorbic acid is present in an amoumt of about 31.75 milligrams per milliliter of said composition.

* * * * *